United States Patent
Kumemura et al.

(10) Patent No.: US 6,656,924 B1
(45) Date of Patent: Dec. 2, 2003

(54) IMMUNOPOTENTIATING COMPOSITIONS

(75) Inventors: Megumi Kumemura, Otsu (JP); Tatsuya Doi, Saga (JP); Takao Saito, Otsu (JP); Tsuneyuki Noda, Otsu (JP); Hiroshi Okamatsu, Suita (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/070,332
(22) PCT Filed: Aug. 24, 2000
(86) PCT No.: PCT/JP00/05655

§ 371 (c)(1),
(2), (4) Date: Feb. 26, 2002

(87) PCT Pub. No.: WO01/16145
PCT Pub. Date: Aug. 3, 2001

(30) Foreign Application Priority Data

Aug. 27, 1999 (JP) .................................. 11-241584

(51) Int. Cl.⁷ ...................... A61K 31/702; A61K 31/70
(52) U.S. Cl. .................... 514/61; 514/889; 514/885; 536/4.1; 536/123.1
(58) Field of Search ................ 514/61, 889, 885; 536/4.1, 123.1

(56) References Cited

FOREIGN PATENT DOCUMENTS

| EP | 0 630 651 | 6/1994 |
| EP | 630651 | 12/1994 |
| JP | 10-179099 | 7/1998 |
| JP | 10-265390 | 10/1998 |
| WO | WO 97/34615 | 9/1997 |

OTHER PUBLICATIONS

Teramoto et al. (Journal of Gastroenterology (1996), 31(1), 33–9).*

* cited by examiner

Primary Examiner—Samuel Barts
Assistant Examiner—Michael C Henry
(74) Attorney, Agent, or Firm—Sughrue Mion, PLLC

(57) ABSTRACT

The invention provides an immunopotentiating composition and to a composition accelerating the production of interferon-γ, both comprising lactosuclose as an active ingredient. In particular, the invention provides such compositions in the form of a foodstuff. Oral administration or ingestion of the compositions enhances biophylaxis mechanism (immunological function) in the digestive tract, thus achieving significant treating and preventing effects on intestinal infections and like diseases.

12 Claims, 1 Drawing Sheet

IMMUNOPOTENTIATING COMPOSITIONS

CROSS-REFERENCE

This is a National stage entry under 35 U.S.C. §371 of Application No. PCT/JP00/05655 filed Aug. 24, 2000; the disclosure of which is incorporated herein by reference.

TECHNICAL FIELD

The present invention relates to an immunopotentiating composition and to a composition accelerating the production of interferon-γ.

BACKGROUND ART

The skin and mucous membrane boundaries between the body and the outside world, and particularly the intestinal and other mucous membranes of the digestive tract, come into contact with many foreign bodies including viruses, bacteria, parasites, disease antigens and food antigens. Therefore, the skin and mucous membranes have immune systems which protect the body by keeping out such foreign bodies. One immune substance which acts to keep out such foreign bodies is immunoglobulin A (IgA). IgA plays an important role in neutralizing toxins of bacteria or viruses, controlling adhesion of bacteria to tissue, and suppressing allergies caused by food antigens. Production of IgA involves the lymphocytes of the Peyer's patch, a lymphatic tissue of the intestines.

When the immune functions of the biological protective systems of the digestive tract mucous membranes are depressed, foreign microorganisms colonize the digestive tract and proliferate, causing digestive tract infections, bacterial diarrhea and the like and resulting in such symptoms as fever, vomiting, diarrhea and abdominal pain. Immune function depression may also be caused by anorexia due to overwork or stress, for example.

Young children, the elderly and people in a weakened condition are particularly vulnerable to external pathogens because their immune systems are depressed. Consequently, substances which act to accelerate production of IgA and maintain it at high levels would be beneficial for such individuals and for the aforementioned digestive tract infection sufferers, particular if administration were in the form of a drink or other foodstuff.

However, there is currently no effective prophylactic or therapeutic drug which acts to accelerate IgA production in cases of depressed gut immune function and intestinal infections. Treatments of bacterial diarrheal diseases are currently limited to fluid infusions for dehydration and administration of antibiotics.

DISCLOSURE OF THE INVENTION

Consequently, the object of the invention is to provide a new digestive immunopotentiating composition for prevention and/or treatment of such intestinal infections and the like, and particularly such a composition in the form of a drink or other foodstuff.

After extensive research aimed at attaining this object, the inventors accomplished the invention upon making the novel discovery that lactosucrose exhibits the desired immunopotentiating effect in humans, and that the administration of lactosucrose can treat and prevent the digestive tract infections and the like.

The invention provides an immunopotentiating composition comprising lactosucrose together with a carrier.

The inventors also found the novel fact that production of interferon-γ(IFN-γ) is accelerated by administration of such a composition.

Consequently, the invention provides a composition accelerating the production of IFN-γ comprising lactosucrose together with a carrier.

The compositions of the invention must contain lactosucrose (hereunder referred to as "LS") as an active ingredient. As used here, the term "lactosucrose" indicates the well-known substance of the following chemical formula, having the chemical name O-β-D-galactopyranosyl-(1→4)-O-α-D-glucopyranosyl-(1←2)-β-D-fructofuranoside.

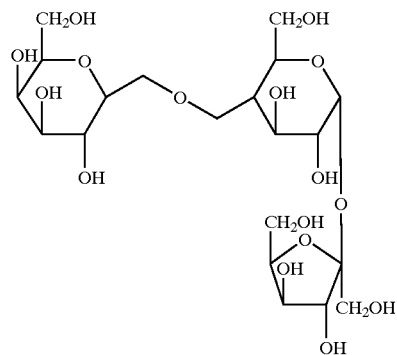

LS can be manufactured by various methods. Such methods include for example the method of applying Aerobacter-derived levansucrase to a solution containing sucrose and lactose as described in Japanese Examined Patent Publication No. S57-58905, the method of applying a fungus of the genus Sporobolomyces, such as for example *Sporobolomyces singularis*, or an extract thereof to a solution containing sucrose and lactose as described in Japanese Unexamined Patent Publication No. S64-85090, or the method of applying a fungus of the genus Rahnella, such as for example *Rahnella aquatilis*, or an extract thereof to a solution containing sucrose and lactose as described in Japanese Unexamined Patent Publication No. H2-35095.

A reaction mixture comprising mainly LS obtained by the aforementioned methods or purified LS prepared therefrom may be used in the composition of the invention.

LS is also known as a vital nutrient (glycogen) which is essential for selective growth of Bifidobacterium in the intestine.

The proportion of LS in the composition of the invention is normally selected from the range of about 0.5 to about 70 g/100 g or preferably about 5 to about 30 g/100

There are no particular limits on the form of the immunopotentiating composition or composition accelerating the production of IFN-γ of the present invention so long as it can be administered orally or ingested. The composition can be provided in various forms including block, liquid, syrup or powder. More specific examples of forms that can be used include foodstuffs such as liquid or powdered sweeteners, beverages such as soft drinks, milk drinks and carbonated drinks, and snacks such as breads, cookies and candies as well as health foods, and medicinal preparations such as bulk powders, powders, liquids, suspensions, tablets and effervescent preparations and the like.

Of these, drinks and effervescent preparations are particularly desirable.

The above-mentioned forms of the composition of the invention may be produced by formulating the active ingredient LS together with food carriers or pharmaceutically acceptable drug carriers suited to the various forms. Food carriers include for example such edible additives as fillers, sweeteners, other carbohydrates, vitamins, flavors and colorings.

More specifically, if for example the composition of the present invention is in food form, considering that a daily allowance (effective dose) of LS is about 1 to about 30 g, the composition is prepared from LS together with suitable food carriers so that the effective dose can be easily ingested. A typical example of a food form is a drink, which can be prepared in the form of an aqueous solution containing 0.5–70 g/100 ml or preferably 5–30 g/100 ml of the active ingredient. The pH of such a drink can also be adjusted to about 4.0 to about 6.5 or preferably about 4.5 to about 6.0 using a pH regulator or buffer or the like.

Typical examples of such pH regulators or buffers include weak acids such as citric acid, tartaric acid, malic acid, lactic acid and carbonic acid, and salts thereof such as sodium citrate, ammonium citrate, sodium tartrate, sodium malate, sodium lactate, calcium lactate, sodium carbonate and sodium hydrogencarbonate. Sodium hydrogenphosphate can also be used as the pH regulator or buffer. These acids or salts thereof can be used either individually or in combinations of two or more. The formulating amount thereof is selected from a range conducive to the above-mentioned pH range of product beverage, but may generally be no greater than about 2% by weight or preferably about 0.05 to about 0.3% by weight of the composition.

Various carbohydrates, sweeteners and other additives can also be added to the composition of the invention when it is in the form of such a drink or other foodstuff, as they are to ordinary beverages and the like. Examples of carbohydrates include glucose, fructose and other monosaccharides; maltose, sucrose and other disaccharides; dextrin, cyclodextrin and other polysaccharides (other than LS); xylitol, erythritol, sorbitol and other sugar alcohols; and sugar esters and the like. Examples of sweeteners include natural sweeteners (Rebaudioside A and other stevia extracts, sormatin, glycyrrhizin and the like) and synthetic sweeteners (saccharin, aspartame and the like). The formulating amount of such carbohydrates or sweeteners is generally no more than about 15% or preferably about 13% by weight of the resulting beverage.

One or two or more of the following additives, for example, may also be added as necessary when formulating the composition of the invention as a foodstuff. Such additives include for example grapefruit, apple, orange, lemon, pineapple, banana, pear and other fruit juices (either concentrated or powdered juices or the like); vitamins and provitamins (retinol palmitate, bisbentiamine, riboflavin, pyridoxine hydrochloride, cyanocobalamin, sodium ascorbate, nicotinamide, calcium pantothenate, folic acid, biotin, cholecalciferol, calcium bitartrate, tocopherol, beta carotene and other water-soluble and fat-soluble vitamins); flavors (lemon flavor, orange flavor, grapefruit flavor, vanilla essence and the like); amino acids, nucleic acids and salts thereof (glutamic acid, sodium glutamate, glycine, alanine, aspartic acid, sodium aspargin, inosinic acid and the like); dietary fibers (polydextrose, pectin, xanthan gum, gum arabic, alginic acid and the like); and minerals and trace elements (sodium chloride, sodium acetate, magnesium sulfate, potassium chloride, magnesium chloride, magnesium carbonate, calcium chloride, dipotassium phosphate, monosodium phosphate, calcium glycerophosphate, sodium ferrous citrate, ammonium ferric citrate, iron citrate, manganese sulfate, copper sulfate, sodium iodide, potassium sorbate, zinc, manganese, copper, iodine, cobalt and the like).

The composition of the invention is prepared by mixing the aforementioned ingredients. There are no particular limits on the method of preparation, and the ingredients may all be mixed in one step as necessary, or when oily and aqueous ingredients are concurrently used the oily ingredients may first be dissolved in a suitable oily vehicle, and then emulsified with an aqueous solution of the aqueous ingredients with the aid of an emulsifier. This emulsification process may be carried out by ordinary methods using ordinary emulsifying dispersion equipment such as a homomixer or high-pressure homogenizer or the like, either in a pass-through or circulating system. The ingredients are ordinarily mixed or emulsified at room temperature, but a heating process may also be employed. The resulting composition of the invention is then packed in suitable containers and sterilized by ordinary methods such as pasteurization, sterile filtration or the like to produce a product.

The composition of the invention can also be processed into effervescent products which can be dissolved or dispersed in water, such as tablets, granules, powder or capsules or the like. Such effervescent products are prepared using sodium hydrogencarbonate and/or sodium carbonate as foaming agents along with a neutralizer. Possible neutralizers include for example citric acid, tartaric acid, fumaric acid, ascorbic acid, lactic acid, malic acid and the like. The proportions of the foaming agent and neutralizer in the total ingredients are preferably be selected from the range of 8–60% by weight of effervescing agent and 10–70% of neutralizer. Such effervescent products can be prepared according to ordinary methods such as direct powder compression or dry or wet granulation compression, optionally with the addition of a suitable amount of potassium carbonate.

There are no particular limits on the ingested or administered dose of the composition of the invention, which is established judiciously according to the intended use or the age, sex, body weight or severity of illness of the intended user, and other factors. When the composition of the invention is in solid form, about 1 to about 30 g of the active ingredient per dose is normally ingested at one time, preferably after dissolution in 30–200 ml of water. When the composition of the invention is in drink or other liquid form, about 30 to about 200 ml is to be taken at a single time. The daily ingested or administered amount of the composition of the invention is preferably such that about 0.5 to about 70 g or preferably about 1 to about 30 g or more preferably about 3 to about 20 g of the active ingredient contained therein is ingested or administered. This ingested or administered amount can be achieved by taking the aforementioned solid or drink form several times a day.

EFFECTS OF THE INVENTION

Upon oral administration or ingestion, the composition of the invention can produce immunopotentiating or IFN-γ production accelerating effects, enhancing the biological defence mechanisms (immune functions) of the digestive tract and effectively preventing and treating intestinal infections and the like.

BEST MODE FOR CARRYING OUT THE INVENTION

Figure 1:
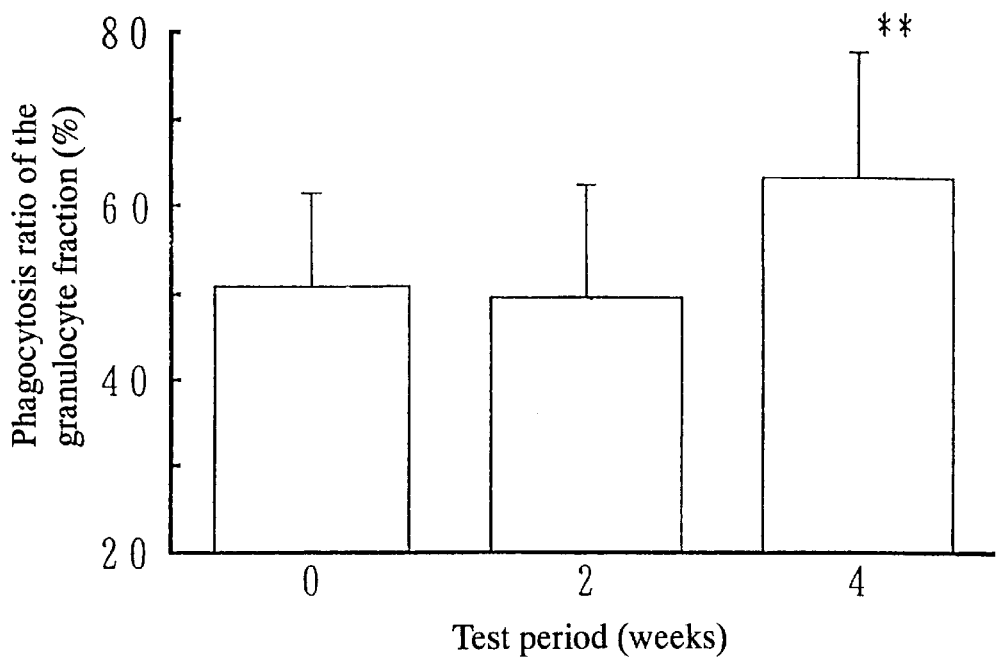
FIG. 1 is a graph showing the phagocytosis rate (%) for the granulocyte fraction of subjects who ingested the composition of the invention in Test Example 2.

For a further detailed description of the invention, examples of preparation of the composition of the invention are given below, followed by test examples of the composition of the invention and LS comprising the same as an active ingredient. Note that "parts" and "%" as used in the examples are all based on weights.

EXAMPLES 1–6

Various material compounds were mixed and dissolved in water according to the recipes shown in Table 1 to provide compositions of the invention. Flavors and/or vitamins could also be included in the compositions of the examples. Each formulation was prepared with water to a total volume of 1000 ml.

TABLE 1

| Example No. | 1 | 2 | 3 | 4 | 5 | 6 |
|---|---|---|---|---|---|---|
| Cation (mEq/l) | | | | | | |
| $Na^+$ | 21 | 15 | 21 | 15 | 8 | 27 |
| $K^+$ | 5 | 5 | 5 | 5 | 4 | 5 |
| $Ca^{2+}$ | 1 | 1 | 1 | 2 | 1 | 1 |
| $Mg^+$ | 0.5 | 0.5 | 0.5 | 0.5 | 0.5 | 0.5 |
| Total | 27.5 | 21.5 | 27.5 | 22.5 | 13.5 | 33.5 |
| Anion (mEq/l) | | | | | | |
| $Cl^-$ | 16.5 | 10.5 | 16.5 | 10.5 | 6.5 | 17.5 |
| Citrate ion ($^{3-}$) | 10 | 10 | 8 | 10 | 4 | 11 |
| Lactate ion ($^-$) | 1 | 1 | 1 | 2 | 1 | 1 |
| Tartrate ion ($^{2-}$) | 0 | 0 | 1 | 0 | 1 | 2 |
| Malate ion ($^{2-}$) | 0 | 0 | 1 | 0 | 1 | 2 |
| Total | 27.5 | 21.5 | 27.5 | 22.5 | 13.5 | 33.5 |
| Rebaudioside A (mg/l) | 80 | 75 | 83 | 73 | 70 | 85 |
| Saccharide Fructose (g/l) | 20 | 18 | 17 | 16 | 15 | 22 |
| Glucose (g/l) | 2 | 1 | 2 | 3 | 2 | 1 |
| Lactosucrose (g/l) | 100 | 50 | 10 | 60 | 30 | 200 |

EXAMPLE 7

The following ingredients (total 5 g) were mixed and directly compressed into tablets, or the various ingredients were weighed, mixed and divided as powders, or else weighed, mixed, granulated, dried and divided as granules to prepare formulated forms of the composition of the invention.

| | |
|---|---|
| LS55P | 34% |
| (as LS | 18.7%) |
| L-ascorbic acid | 21% |
| L-tartaric acid | 20% |
| Sweetener | q.s. |
| Sodium hydrogencarbonate | 21% |
| Sodium chloride | q.s. |
| Potassium carbonate | 0.5% |
| Flavor and coloring | Trace |
| Total | 100% |

The "LS55P" mentioned above is a powder containing 55% LS.

EXAMPLES 8–10

Tablet, powder or granulated formulations of the composition of the invention containing the following ingredients were prepared as in Example 7 above. (Recipe for Example 8)

| | |
|---|---|
| LS55P | 40% |
| (as LS | 22%) |
| L-ascorbic acid | 10% |
| L-tartaric acid | 23% |
| Sweetener | q.s. |
| Sodium hydrogencarbonate | 22% |
| Sodium citrate | q.s. |
| Potassium carbonate | 0.4% |
| Flavor, coloring | Trace |
| Total | 100% (total 5 g) |
| (Recipe for Example 9) | |
| LS55P | 40% |
| (as LS | 22%) |
| L-ascorbic acid | 11% |
| L-tartaric acid | 23% |
| Sweetener | q.s. |
| Sodium hydrogencarbonate | 22% |
| Ammonium citrate | 0.8% |
| Cyanocobalamin | Trace |
| Sodium citrate | Trace |
| Potassium carbonate | 0.4% |
| Flavor, coloring | Trace |
| Total | 100% (total 4.6 g) |
| (Recipe for Example 10) | |
| LS55P | 40% |
| (as LS | 22%) |
| L-tartaric acid | 29% |
| Sweetener | q.s. |
| Sodium hydrogencarbonate | 24% |
| Ammonium ferric citrate | 3.6% |
| Cyanocobalamin | Trace |
| Potassium carbonate | 0.5% |
| Flavor, coloring | Trace |
| Total | 100% (total 4 g) |

EXAMPLES 11–18

Effervescent tablet forms of the composition of the invention according to the recipes shown in Table 2 below were prepared in the similar manner as in Examples 7–10.

TABLE 2

| | Example No. | | | | | | | |
|---|---|---|---|---|---|---|---|---|
| Ingredient | 11 | 12 | 13 | 14 | 15 | 16 | 17 | 18 |
| LS55P (%) | 40 | 30 | 40 | 60 | 50 | 35 | 45 | 35 |
| (as LS | (22) | (16.5) | (22) | (33) | (27.5) | (19.3) | (24.8) | (19.3) |

TABLE 2-continued

| Ingredient | 11 | 12 | 13 | 14 | 15 | 16 | 17 | 18 |
|---|---|---|---|---|---|---|---|---|
| L-ascorbic acid | 11 | 16 | 10 | 8 | 10 | 10 | 10 | 13 |
| L-tartaric acid | 23 | 23 | 23 | 13 | 19 | 20 | 20 | 25 |
| Sweetener | q.s. | q.s. | q.s. | q.s. | q.s. | q.s. | q.s. | q.s. |
| Sodium hydrogencarbonate | 22 | 22 | 23 | 15 | 15 | 20 | 20 | 23 |
| Ammonium ferric citrate | 0.8 | 0.8 | 1.0 | 0.8 | 0.8 | — | — | 0.7 |
| Sodium ferrous citrate | — | — | — | — | — | 1.2 | — | — |
| Iron citrate | — | — | — | — | — | — | 0.8 | — |
| Sodium citrate | q.s. | q.s. | q.s. | q.s. | q.s. | q.s. | q.s. | q.s. |
| Total weight (g) | 4.6 | 4.6 | 4.7 | 4.6 | 4.6 | 4.7 | 4.7 | 5.4 |

EXAMPLES 19–25

The ingredient materials (mg) shown below in Table 3 were mixed and directly compressed to provide chewable tablets.

TABLE 3

| Ingredient | 19 | 20 | 21 | 22 | 23 | 24 | 25 |
|---|---|---|---|---|---|---|---|
| LS75P (mg) | — | — | — | 700 | 3330 | 600 | 350 |
| (as LS mg) | | | | (525) | (2498) | (450) | (263) |
| LS55P (mg) | 1800 | 3600 | 4620 | — | — | — | — |
| (as LS mg) | (990) | (1980) | (2541) | | | | |
| Sugar ester (mg) | 40 | 80 | 841 | 20 | 80 | 15 | 7 |
| Polydextrose (mg) | 150 | 400 | 300 | 100 | 300 | 60 | 60 |
| Sucrose (mg) | 100 | 200 | 200 | 20 | 200 | 80 | 20 |
| Vitamin C (mg) | 150 | 320 | 200 | 20 | 200 | — | — |
| Powdered orange juice (mg) | 80 | 150 | — | — | 100 | 20 | 5 |
| Powdered lemon juice (mg) | — | — | 84 | 40 | — | 10 | 5 |
| Tartaric acid (mg) | — | — | — | — | 460 | 95 | 50 |
| NaHCO$_3$ (mg) | — | — | — | — | 500 | 100 | 50 |
| K$_2$CO$_3$ (mg) | 30 | 40 | 40 | 40 | 30 | 8 | 8 |
| Perfume & sweetener | q.s. | q.s. | q.s. | q.s. | q.s. | q.s. | q.s. |
| Total weight (mg) | 2400 | 4950 | 5580 | 1000 | 5200 | 1000 | 5000 |

The "LS75P" mentioned above is a powder containing 75% LS.

EXAMPLES 26–34

The ingredients shown in Table 4 below were mixed and made up to 100 ml with water to provide health drink forms of the composition of the invention.

TABLE 4

| Ingredient (in 100 ml) | 26 | 27 | 28 | 29 | 30 |
|---|---|---|---|---|---|
| β-Carotene (mg) | 3 | 5 | 10 | 15 | 1 |
| Polydextrose (g) | 5 | 3 | 5 | 7 | 4 |
| Emulsifier (mg) | 6 | 10 | 20 | 30 | 5 |
| Oil (mg) | 100 | 90 | 80 | 120 | 50 |
| Fructose (g) | — | 15 | 10 | — | 15 |
| Citric acid (mg) | 200 | 400 | 100 | 300 | 50 |
| Tartaric acid (mg) | — | — | 50 | — | 50 |
| Lactic acid (mg) | — | — | — | — | 50 |
| Ascorbic acid (mg) | 300 | 200 | 100 | 50 | 30 |
| Tocopherol (mg) | 10 | 5 | 10 | 20 | 20 |
| LS55P (g) | 2 | 5 | 10 | 3 | 8 |
| (as LS mg) | (1.1) | (2.75) | (5.5) | (1.65) | (4.4) |
| Perfume & sweetener | q.s. | q.s. | q.s. | q.s. | q.s. |

| Ingredient (in 100 ml) | 31 | 32 | 33 | 34 |
|---|---|---|---|---|
| β-Carotene (mg) | 2 | 30 | 5 | 3 |
| Polydextrose (g) | 2 | 10 | 20 | 20 |
| Emulsifier (mg) | 6 | 20 | 15 | 8 |
| Oil (mg) | 50 | 200 | 70 | 60 |
| Fructose (g) | 15 | 15 | 5 | 10 |
| Citric acid (mg) | 20 | — | — | — |
| Tartaric acid (mg) | 10 | 100 | 200 | — |

TABLE 4-continued

| | | | | |
|---|---|---|---|---|
| Lactic acid (mg) | 10 | 100 | — | 200 |
| Ascorbic acid (mg) | 150 | 200 | 1000 | 50 |
| Tocopherol (mg) | 0.5 | 20 | 10 | 5 |
| LS55P (g) | 7 | 5 | 12 | 10 |
| (as LS mg) | (3.85) | (2.75) | (6.6) | (5.5) |
| Perfume & sweetener | q.s. | q.s. | q.s. | q.s. |

Propylene glycol fatty acid ester was used as the emulsifier, and safflower oil as the oil.

EXAMPLES 35–45

The ingredients shown in Table 5 below were mixed and made up to 100 ml with water to provide beverage forms of the composition of the invention.

The gas volume values in the table indicate carbon dioxide content, with 1 being a volume of dissolved carbon dioxide gas equal to the volume of the solution; the higher the value, the greater the carbon dioxide content.

TABLE 5

| Ingredient | Example No. | | | | | |
|---|---|---|---|---|---|---|
| (in 100 ml) | 35 | 36 | 37 | 38 | 39 | 40 |
| Lactosucrose (g) | 3 | 12 | 9 | 1 | 8 | 2 |
| Isomerized sugar (g) | 8 | — | — | 7 | 7 | 8 |
| Purified sucrose (g) | — | 1 | 8 | 3 | 7 | 5 |
| Fructose (g) | 2 | 6 | — | 1 | — | — |
| Glucose (g) | 2 | 2 | — | — | 2 | — |
| Citric acid (mg) | 3 | 2 | — | — | 8 | — |
| Tartaric acid (mg) | — | 2 | — | 2 | — | — |
| Malic acid (mg) | 4 | — | 8 | — | 5 | — |
| Lactic acid (mg) | 8 | — | — | 2 | — | 20 |
| Sodium citrate (mg) | 20 | 30 | 10 | — | 80 | — |
| Sodium tartrate (mg) | 60 | — | — | 60 | 25 | 70 |
| Sodium malate (mg) | — | 80 | 150 | — | — | 100 |
| Calcium lactate (mg) | — | — | — | — | 15 | 10 |
| Sodium chloride (mg) | — | — | 4 | — | 1 | 1.5 |
| Potassium chloride (mg) | — | 3 | — | 2 | — | — |
| Magnesium chloride (mg) | 2 | — | 1 | — | — | — |
| Fruit juice (%) | 3 | — | 1 | 0.5 | 0.1 | — |
| Perfume & sweetener | q.s. | q.s. | q.s. | q.s. | q.s. | q.s. |
| Gas volume | — | — | — | — | — | 3.0 |
| pH | 5.0 | 6.3 | 5.8 | 4.9 | 5.8 | 5.3 |

| Ingredient | Example No. | | | | |
|---|---|---|---|---|---|
| (in 100 ml) | 41 | 42 | 43 | 44 | 45 |
| Lactosucrose (g) | 4 | 10 | 15 | 7 | 13 |
| Isomerized sugar (g) | 5 | — | — | 9 | — |
| Purified sucrose (g) | 3 | — | — | — | — |
| Fructose (g) | 3 | — | — | — | 60 |
| Glucose (g) | 3 | — | — | 2 | 4 |
| Citric acid (mg) | — | 2 | 5 | — | — |
| Tartaric acid (mg) | — | — | — | 10 | — |
| Malic acid (mg) | 4.5 | — | — | — | — |
| Lactic acid (mg) | — | — | — | 10 | — |
| Sodium citrate (mg) | — | 100 | 55 | 70 | — |
| Sodium tartrate (mg) | — | — | — | 30 | 20 |
| Sodium malate (mg) | 45 | — | 10 | — | 50 |
| Calcium lactate (mg) | — | — | — | — | 5 |
| Sodium chloride (mg) | — | — | 2 | — | — |
| Potassium chloride (mg) | 5 | — | 1 | 1 | — |
| Magnesium chloride (mg) | — | — | 1 | — | — |
| Fruit juice (%) | — | — | — | 2 | 0.3 |
| Perfume & sweetener | q.s. | q.s. | q.s. | q.s. | q.s. |
| Gas volume | 2.0 | 2.5 | 2.3 | 3.3 | 1.5 |
| pH | 5.5 | 5.6 | 6.4 | 5.6 | 5.9 |

TEST EXAMPLE 1

Performed as follows, this experiment tested the effects on intestinal flora and immune function of ingestion of the composition of the invention in drink form according to the double-blind comparison method with a placebo drink as the control.

1. Subjects: 28 adult males
2. Test design: Double-blind comparison test with a placebo drink as the control
3. Group composition:
    Invention group: Group ingesting the drink of the invention (n=14)
    Control group: Group ingesting a placebo drink (n=14)
4. Test substances:
    Drink of the invention:
    A solution prepared by dissolving 5 g of lactosucrose (LS) in 50 ml of water (1).
    Placebo drink:
    Prepared in the same way using sugar in place of LS of the drink of the invention.
5. Dosage: 1 per day (total 50 ml) taken at bedtime. Taken for 6 weeks.
6. Measurements: Intestinal flora and fecal IgA concentrations
7. Feces collection methods:
    Fresh feces were collected before ingestion of the test substances and after 6 weeks of ingestion. Feces excreted after waking on the collection day was collected in sealable polyethylene bags, and the bags were sealed taking extreme care that no air remained inside and stored on ice in polypropylene feces collection containers. The collected feces was weighed and well mixed, and intestinal flora and IgA volume were measured. Part of the feces was stored at −80° C. for purposes of measuring IgA volume.
8. Measurement of intestinal flora:
    Intestinal flora was investigated according to the methods of Mitsuoka et al (Tomotari Mitsuoka, "Common Intestinal Flora", *Rinsho Kensa* (Clinical Test), 23(4): 320–334 (1979)), with 3 kinds of nonselective medium (BL agar, EG agar, Tryptycase soy blood agar) and 11 types of selective medium (BS agar, NBGT agar, ES agar, modified VS agar, Neomycin Nagler agar, modified LBS agar, DHL agar, TATAC agar, PEES agar, Potato dextrose agar, GE agar) as the preparative media. The compositions of these media are given in "Common Intestinal Flora", Tomotari Mitsuoka, *Rinsho Kensa* (Clinical Test), 23(4): 320–334 (1979).

About 1.0 g of fresh feces was first accurately weighed and suspended in 9 ml of anaerobic diluent (prepared as described in the aforementioned reference), then diluted sequentially 10 times with the diluent in a carbon dioxide gas atmosphere to prepare $10^1$–$10^8$ dilutions. The $10^6$, $10^7$ and $10^8$ dilutions thus prepared were smeared on the BL and EG agar media, the $10^5$ $10^6$ and $10^7$ dilutions on the Tryptycase soy blood agar medium and the $10^1$, $10^3$, $10^5$ and $10^7$ dilutions on the other selective media, each in the amount of 0.05 ml. Next, the BL, EG, BS, NBGT, ES, modified VS, Neomycin Nagler and modified LBS agars were placed in anaerobic jars, and anaerobically cultured for 48 hours at 37° C. by the steel wool method following carbon dioxide gas replacement. The Tryptycase soy blood and DHL agars were cultured in the similar manner for 24 hours at 37° C., and the TATAC, PEES, Potato dextrose and GE agars for 48 hours.

Following culture, the number of colonies on each medium was counted, and the genus revel was identified according to the properties of the colonies, gram staining, spore production, aerobic growth and morphology under a microscope. The results were expressed relatively as logarithmic bacterial numbers per 1 g of feces (log10CFU/g wet feces).

9. Measurement of fecal IgA concentrations:

(1) Preparation of Fecal IgA Measurement Samples Feces samples stored at −80° C. were freeze dried, and 2.0 ml of 0.1 M carbonate buffer (pH 9.6) was added to 0.2 g of dried feces and shaken, then centrifuged for 10 minutes at 1500 rotation per minute, and the supernatant was adjusted to pH 7.5 for use as the IgA measurement sample.

(2) Measurement of IgA Concentrations in Fecal IgA Measurement Samples

IgA concentrations were measured by ELISA, according to the methods of Tsuyuki et al (Tsuyuki, Shigeo, Shoji Yamazaki, Hiroshi Uemura, Masanobu Kimura, Hiroshi Kawashima & Yuki Ueda, "Measurement of IgA antibodies and total IgA in mouse bile and small intestinal contents by the ELISA method", *Bifidus* 2: 9–13 (1988)).

IgA antibodies were measured as follows. Namely, the antigen used was unlabeled mouse-derived anti-human IgA (25 µg/ml, 200 µl), which was injected into the wells and left overnight at 4° C. Wells injected with an equal amount of buffer in place of the antigen were used as controls.

The following day, the solution was sucked from the wells and a 1% BSA solution (0.1 M carbonic acid buffer, 200 µl) was added as a spacer and reacted for 60 minutes at 37° C. Next, the fecal IgA measurement samples (40 µl) were added to the antigen-treated and control wells, and reacted for 45 minutes at 37° C. Following this reaction peroxydase labeled mouse-derived anti-human IgA (1000×diluted, 40 µl) was added, and reacted for 45 minutes at 37° C. Sigma Fast ODP (Sigma Co., 200 µl) was then added to color for 15 minutes, the reaction was stopped with 3M HCl (50 ml), and absorbance (490 nm) was measured.

IgA concentrations in the samples were obtained in such a manner that a working curve was prepared from an sIgA sample (purified human secretory IgA 5 mg; Capple Co.), and IgA concentrations in the samples calculated from the working curve were converted to concentrations per 1 g of dried feces.

10. Statistical analysis:

Mean values and standard deviations for each group were calculated from the values before ingestion the test substance and after 6 weeks of ingestion. Comparison of groups was done by variance analysis including repetition, with a significance level of 5% or less. The results of the test are as shown in Table 6 below.

TABLE 6

| | Fecal IgA concentration (mg/g · dry wt) | Intenstinal flora (log10CFU/g wet feces) | Occupation rate of Bifidobacterium (%) |
|---|---|---|---|
| Invention drink ingestion group | | | |
| n | 14 | 13 | 13 |
| Mean ± SD | | | |
| Before Ingestion | 3.9 ± 3.2 | 9.5 ± 0.7 | 19.6 ± 15.2 |

TABLE 6-continued

| | Fecal IgA concentration (mg/g · dry wt) | Intenstinal flora (log10CFU/g wet feces) | Occupation rate of Bifidobacterium (%) |
|---|---|---|---|
| After 6 Weeks of Ingestion | 6.9 ± 5.4 | 10.1 ± 0.7 | 32.1 ± 15.2 |
| Placebo drink ingestion group | | | |
| n | 14 | 12 | 12 |
| Mean ± SD | | | |
| Before Ingestion | 5.6 ± 7.0 | 9.8 ± 0.6 | 23.5 ± 12.6 |
| After 6 Weeks of Ingestion | 4.4 ± 3.1 | 9.8 ± 0.6 | 18.8 ± 9.2 |

The following is evident from the results shown in Table 6.

1. In the invention drink ingestion group, ingestion of the drink of the ingestion resulted in increased numbers of Bifidobacterium, (9.5±0.7→10.1±0.7 log10 CFU/g wet feces, Paired t-test; P=0.013). By contrast, there was no change in the placebo drink ingestion group (9.8±0.6→9.8±0.6 log10 CFU/g wet feces) Consequently, there was a significant difference between the groups in the change in numbers of Bifidobacterium.

2. In the invention drink ingestion group, ingestion of the drink of the invention resulted in an increased occupation rate of Bifidobacterium (19.6±15.2→32.1±15.2%, Paired t-test; P=0.001). By contrast, there was a tendency to decrease in the placebo drink ingestion group (23.5±12.6→18.8±9.2%, Paired t-test; P=0.110), so there was also a significant difference between the groups in terms of change in Bifidobacterium occupation rate.

3. Fecal IgA concentrations rose significantly in the invention drink ingestion group (3.9±3.2→6.9±5.4 mg/g dry wt, Paired t-test, P=0.014). By contrast, there was no change in the placebo drink ingestion group (5.6±7.0→4.4±3.1 mg/g dry wt), so there was a significant difference between the groups in terms of change in fecal IgA concentration.

This shows that fecal IgA concentrations rose as a result of ingestion of the tested drink of the invention. It is therefore clear that the drink of the invention promotes production of IgA in the digestive tract.

The inventors also confirmed that cecal IgA concentrations also rise significantly in guinea pigs who ingested LS in the similar manner.

TEST EXAMPLE 2

This experiment was performed as follows to test the effects that the composition of the invention (the active ingredient LS) on immune indicators when ingested by healthy individuals.

1. Subjects

The subjects were 20 healthy adults who had not taken any antibiotics within the previous month.

2. Test substances and ingestion conditions

The subjects ingested the drink of the invention (a solution of 5 g LS dissolved in 50 ml water) twice a day (at 10:00 a.m. and 3:00 p.m.) for 4 weeks.

3. Test methods

The subjects were given the test substance to drink, and blood was taken on the first day of ingestion (Week 0) and after 4 weeks of ingestion (Week 4). The subjects fasted after 9:00 p.m. on the days before blood and feces were collected. During the test period, they were asked to avoid excessive eating and drinking and ingestion of fermented foods. They were also asked to refrain from taking medicines during the test period.

4. Evaluation items and methods (1) Serum transferrin: by nepherometry (2) Phagocytosis of the granulocyte fraction:

20 $\mu$l of fluorescent beads (2 $\mu$m florescent labeled beads, Polyscience #1 8604, Lot No. 425844) were added to 1 ml of glucose medium (1:1:8 volume ratio mixture of Solution A below, Solution B below and sterile water), and washed by centrifugation for 30 minutes at 11000 rpm.

Glucose medium composition

Solution A: 1.01 M NaCl 0.31 M $CH_3COONa$ 0.04 M KCl 0.04 M $CaCl_2$ 0.02 M $MgCl_2$ Solution B: 0.07 M Glucose The resulting sediment was suspended in 1 ml of the same glucose medium, and ultrasonically treated to obtain a uniform bead liquid. 100 $\mu$l of these fluorescent beads were added to 100 $\mu$l of peripheral blood taken with heparin from the test subjects, and incubated with shaking for 0, 5, 10 and 30 minutes at 37° C. After the reaction was finished, 2 ml of a liquid consisting of a hemolytic dissolved in an equal quantity of buffer (Facs Lysing buffer, Becton Dickinson Co., Cat. No. 349202) was added to completely hemolyze the erythrocytes, and measurement was carried out after ice cooling. The samples were measured with a flow cytometer (Coulter Epics XL-MCL System II). A gate was assigned to the granulocyte fraction and set to detect the fluorescence-emitting phagocytes as a peak, and this phagocytosis rate was analyzed.

(3) Eosinophils: by microscopy

5. Statistical treatment

All data were shown as mean±standard deviation, and after randomized block layout they were tested by Dunnett's multiple comparison and significant differences were evaluated. The significance level was 5% or less.

6. Results (1) Serum Transferrin

The results obtained are shown in Table 7.

TABLE 7

|  | The first day of ingestion (Week 0) | After 4 weeks of ingestion (Week 4) |
| --- | --- | --- |
| Serum transferring (mg/dl) | 285 ± 30 | 295 ± 34✕ |

Mean ± S.D., n = 20 (week 0), 17 (week 4)
✕:p < 0.05 vs. week 0

The results in Table 7 show that serum transferrin concentrations were significantly higher after 4 weeks of ingestion compared to Week 0, with a significance level of less than 5%.

(2) Phagocytosis of the Granulocyte Fraction

The results are as shown in FIG. 1 (vertical axis= phagocytosis rate of granulocyte fraction (%), horizontal axis =test period (weeks)), and indicate that the mean±S.D. (30-minute reaction values) for phagocytosis rate of the granulocyte fraction were 50.8±10.8% at Week 0 and 63.6±14.1% at Week 4, a significant rise from Week 0 to Week 4 with a significance rate of less than 1%.

(3) Blood Eosinophils

The results are shown in Table 8.

The results of general blood tests (leukocytes, neutrophils, basophils, lymphocytes and monocytes) performed at the same time are also shown in Table 8.

TABLE 8

|  | The first day of ingestion (Week 0) | After 4 weeks of ingestion (Week 4) |
| --- | --- | --- |
| Leukocytes (counts/$\mu$l) | 5443 ± 1604 | 5536 ± 2370 |
| Neutrophils (%) | 59.9 ± 11.0 | 59.9 ± 6.7 |
| Basophils (%) | 1.0 ± 0.7 | 1.0 ± 0.5 |
| Eosinophils (%) | 4.7 ± 3.9 | 3.2 ± 2.0✕ |
| Lymphocytes (%) | 28.9 ± 9.5 | 29.2 ± 5.8 |
| Monocytes (%) | 5.9 ± 2.1 | 6.7 ± 1.2 |

Mean ± S.D., n = 20 (week 0), 17 (week 4)
✕:p < 0.05 vs. week 0

The results in this table shown that blood eosinophils were significantly lower in Week 4 than in Week 0, with a significance level of less than 5%.

7. Discussion

The results above show that ingestion of the composition of the invention results in increased serum transferrin and phagocytosis of the granulocytes, which are critical to preventing infection, and that therefore the composition of the invention acts to enhance the host's protective functions against infection. They also suggest that since ingestion of the composition of the invention results in decreased blood eosinophils, the composition of the invention has the potential to suppress allergic reactions.

TEST EXAMPLE 3

This experiment was performed as follows using heritable diabetic model animals to test the effects of feeding of the composition of the invention on intestinal immunity.

1. Test Animals 4-week-old LETO rats and OLETF rats (10 each) were used. OLETF embryos were deposited on Aug. 24, 1994 with American Type Culture Collection as ATCC No. 72016. LETO rats are preserved and available for purchase at Otsuka Seiyaku Tokushima Experimental Animal Facility.

2. Animal Keeping Conditions

After delivery, the rats were quarantined for 1 week. During this period they fed MF solid feed (Oriental Yeast Co.) adlibitium and tap water. They were kept in stainless steel cages, one rat per cage, on a light/dark cycle with light from 7:00 to 19:00.

During the test period, a low-fiber (3%), high-fat (5% corn oil +10% beef fat) feed was prepared according to AIN76 composition (American Institute of Nutrition (1977) Report of the American Institute of Nutrition ad hoc committee on standards for nutrition studies., *J. Nutri.*, 107: 1340–1348) as the control feed, and feed with part of the sucrose/corn starch mixture of the control feed replaced by LS to give the feed a 5% LS content as the feed of the invention (feed containing LS). The compositions of the feeds were as shown in Table 9 below.

TABLE 9

| Ingredient (g/100 g feed) | Control feed | Invention feed |
| --- | --- | --- |
| Casein | 20.00 | 20.00 |
| Corn starch/Sucrose (3:10) | 57.20 | 52.20 |
| Corn oil | 5.00 | 5.00 |
| Beef fat | 10.00 | 10.00 |
| Cellulose | 3.00 | 3.00 |
| AIN76 mineral composition | 3.50 | 3.50 |
| AIN76 vitamin composition | 1.00 | 1.00 |
| DL-Methionin | 0.30 | 0.30 |
| LS | — | 5.00 |
| kcal | 444 | 424 |

3. Test Groups

The test groups (type of animals, feed, number of animals) were as follows.

| Group | Animals | Feed | Number of animals |
| --- | --- | --- | --- |
| 1 | LET0 rats | Control feed | 10 |
| 2 | LET0 rats | Feed of the invention | 10 |
| 3 | 0LETF rats | Control feed | 10 |
| 4 | 0LETF rats | Feed on the invention | 10 |

4. Test Schedule

The animals were kept on control feed for 2 weeks after the end of quarantine. At the end of this period the LETO and OLETF rats were assigned to the aforementioned groups in such a way that all groups had the same mean body weight. After group assignment the test feeds were introduced (at 7 weeks of age), and the rats were kept thereafter on the test feeds for 22 weeks.

5. Dissection

After completion of 22 weeks (29 weeks of age), the rats were opened abdominally under ether anesthesia, blood was taken from the abdominal inferior vena cava, and the rats were sacrificed by bleeding. The inferior vena cava blood was centrifuged for 15 minutes at 3000 rotations per minute, and the serum was separated out and stored at −80° C. After sacrificing, the small intestines of three rats from each group were used to prepare lymphocytes.

6. Preparation of Lymphocytes

Small intestinal Peyer's patch lymphocytes were prepared by the enzyme method using Bacillus-derived protease (Boehringer-Mannheim Corp. "Dispase II"). Peyer's patch cells were isolated according to the methods of Fragaski et al (Fragaski et al., *Journal of Immunological Methods* 48, 33–44 (1989)). After sacrificing, the area from the superior part of the duodenum to the terminal part of the ileum was sterilely removed. After careful washing with sterile saline, a syringe was used to send sterile saline through the intestines to wash out the contents. The Peyer's patches were cut out onto sterile gauze laid on top of ice. The excised Peyer's patches were placed on imperfect RPMI1640 medium (RPMI1640 containing 10 $\mu$g/ml gentamicin). All the Peyer's patches obtained were enzyme treated for 40 minutes at 37° C. while being agitated with a stirrer in a liquid (enzyme liquid) medium (Joklik-modified MEM) containing 1.5 mg/ml Dispase. The cells began to separate were collected and the same enzyme liquid was added again. This process was repeated 3–4 times. The completely isolated cells were centrifuged at 350 g×10 minutes below 4° C., washed in PBS and suspended in the specified medium, and the number of cells were measured on an erythrocytometer.

The Peyer's patches of three rats from each group were pooled, and lymphocytes prepared.

7. Culture of Lymphocytes

The lymphocytes were prepared to a cell count of $1\times10^6$ cells/ml in RPMI1640 (containing 2mM L-glutamine, 50 $\mu$M mercaptoethanol, 100 U/ml penicillin, 100 $\mu$g/ml streptomycin and 10% FCS). 1 ml/well of lymphocyte suspension was cultured under stimulation of 5.0 $\mu$g/ml ConA (Concanavalin A: derived from *Canavalia ensiformis*, Sigma Co.) as the mitogen in 24-well plates for cell culture (FALCON 3047).

Antibody production testing was performed by culturing for 7 days at 37° C. in 5% $CO_2$, and cytokine production testing by culturing for 3 days under the same conditions. One well per sample was cultured in the case of spleen lymphocytes and 3 wells per sample in the case of Peyer's patch lymphocytes.

Upon completion of culture, the plates were centrifuged for 10 minutes at 1600 rotations per minute, and supernatant was collected. The collected supernatant was stored frozen at −20° C. until the various measurements.

8. Measurement of Cytokines

IFN-$\gamma$ in the lymphocyte culture supernatant was measured by the ELISA method using a commercial measurement kit.

9. Statistical Treatment

The results were shown as mean±standard deviation. For the cytokine concentrations, the groups were compared by one-way layout variance analysis followed by Fisher's Protected LSD multiple comparison. Statistical treatment was not done in the case of Peyer's patch cells because samples were pooled for each group. The significance level was less than 5%.

10. Results

Figure 2:
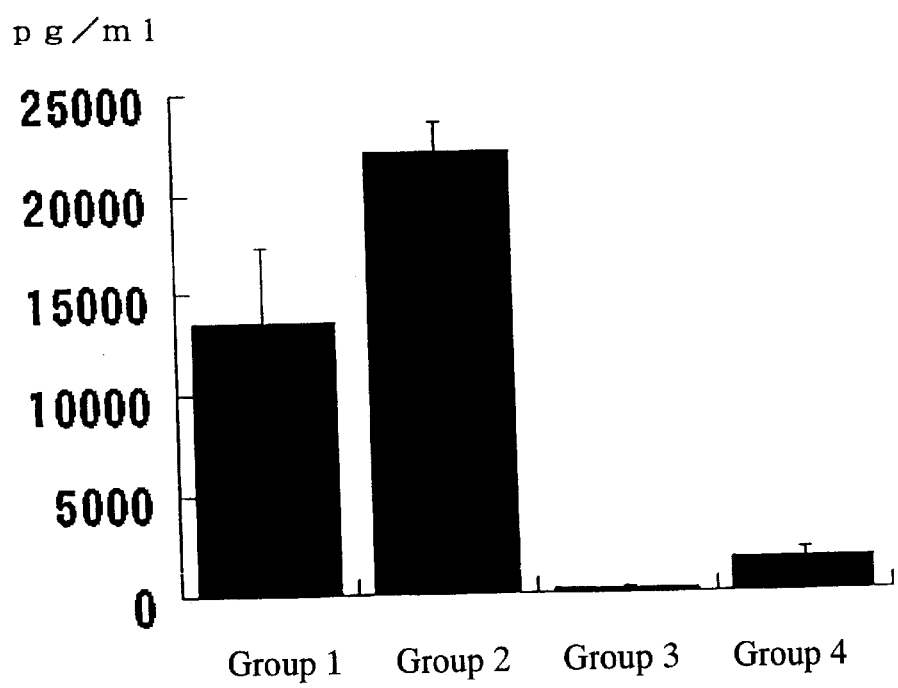
FIG. 2 is a graph showing results for IFN-γ production (pg/ml) by the Peyer's patch lymphocytes of experimental rats who were given the composition of the invention in Test Example 3.

The results for IFN-$\gamma$ production from culture of the Peyer's patch lymphocytes are shown in FIG. 2.

From these results, it is clear that compared to the control feed groups (Groups 1 and 3), both the LETO and OLETF rats in the groups ingesting feed with the composition of the invention (Groups 2 and 4) exhibited higher IFN-$\gamma$ concentrations.

What is claimed is:

1. A method of immunopotentiation of a patient comprising administering to a patient in need of such immunopotentiation, a pharmaceutically effective amount of lactosucrose.

2. The method of claim 1, wherein said lactosucrose is administered in an amount of from 1–30 g/day.

3. A The method of claim 1, wherein said immunopotentiation is acceleration of the production of interferon-$\gamma$ in said patient.

4. The method of claim 3, wherein said lactosucrose is administered in an amount of from 1–30 g/day.

5. A method of inhibiting intestinal infections in a patient comprising administering to a patient in need of such, a pharmaceutically effective amount of lactosucrose.

6. The method of claim 5, wherein said lactosucrose is administered in an amount of from 1–30 g/day.

7. A method of treating intestinal infections comprising administering to a patient in need of such, a pharmaceutically effective amount of lactosucrose.

8. The method of claim 7, wherein said lactosucrose is administered in an amount of from 1–30 g/day.

9. The method of claim 1, wherein said administering is by ingestion.

10. The method of claim 2, wherein said administering is by ingestion.

11. The method of claim 5, wherein said administering is by ingestion.

12. The method of claim 7, wherein said administering is by ingestion.

* * * * *